United States Patent
Koppel et al.

(10) Patent No.: US 6,507,634 B1
(45) Date of Patent: Jan. 14, 2003

(54) SYSTEM AND METHOD FOR X-RAY REFLECTOMETRY MEASUREMENT OF LOW DENSITY FILMS

(75) Inventors: Louis N. Koppel, San Jose, CA (US); William Johnson, Livermore, CA (US)

(73) Assignee: Therma-Wave, Inc., Fremont, CA (US)

( * ) Notice: Subject to any disclaimer, the term of this patent is extended or adjusted under 35 U.S.C. 154(b) by 0 days.

(21) Appl. No.: 10/067,604

(22) Filed: Feb. 4, 2002

Related U.S. Application Data

(60) Provisional application No. 60/323,255, filed on Sep. 19, 2001.

(51) Int. Cl.⁷ .............................................. G01N 23/06
(52) U.S. Cl. ....................................................... 378/54
(58) Field of Search ..................................... 378/54–56

(56) References Cited

U.S. PATENT DOCUMENTS

| | | | |
|---|---|---|---|
| 5,042,951 A | 8/1991 | Gold et al. | 356/369 |
| 5,042,952 A | 8/1991 | Opsal et al. | 356/432 |
| 5,412,473 A | 5/1995 | Rosencwaig et al. | 356/351 |
| 5,619,548 A | 4/1997 | Koppel | 378/70 |
| 5,949,847 A * | 9/1999 | Terada et al. | 378/90 |
| 6,434,217 B1 * | 8/2002 | Pickelsimer et al. | 378/89 |

FOREIGN PATENT DOCUMENTS

| | | | | |
|---|---|---|---|---|
| WO | WO 92/08104 | 5/1992 | .......... | G01B/11/24 |
| WO | WO 00/57127 | 9/2000 | .......... | G01B/11/06 |
| WO | WO 01/71325 | 9/2001 | .......... | G01N/23/00 |

OTHER PUBLICATIONS

K. Sakurai et al., "Fourier Analysis of Interference Structure in X–Ray Specular Reflection from Thin Films," *Jpn. J. Appl. Phys.*, vol. 31. Part 2, No. 2A, Feb. 1, 1992, pp. L113–L115.

K.N. Stoev et al., "Review on grazing incidence X–ray spectrometry and reflectometry,"*Spectrochimica Acta Part B*, vol. 54, 1999, pp. 41–82.

N. Wainfan et al., "Density Measurements of Some Thin Copper Films," *Journal of Applied Physics*, vol. 30, No. 10, Oct. 1959, pp. 1604–1609.

J.P. Sauro et al., "Some Observations on the Interference Fringes Formed by X Rays Scattered from Thin Films," *Physical Review*, vol. 143, No. 1, Mar. 1966, pp. 439–443.

K. Sakurai et al., "Analysis of thin films by X–ray scattering at grazing incidence," *Spring–8 User Experiment Report No. 2 (1998 A)*, Mar. 1999, p. 162.

J.M. Grimal et al., "X–ray reflectivity: a new tool for the study of glass surfaces," *Journal of Non–Crystalline Solids*, vol. 196, 1996, pp. 128–133.

P. Polouček et al., "X–ray reflectivity analysis of thin complex Langmuir–Blodgett films," *Journal of Physics D: Applied Physics*, vol. 34, 2001, pp. 450–458.

C.E. Bouldin et al., "Thermal expansion of coefficients of low–$k$ dielectric films from Fourier analysis of x–ray reflectivity," *Journal of Applied Physics*, vol. 88, No. 2, Jul. 15, 2000, pp. 691–695.

(List continued on next page.)

*Primary Examiner*—Craig E. Church
(74) *Attorney, Agent, or Firm*—Stallman & Pollock LLP

(57) ABSTRACT

A metrology system and method for measuring the thickness of thin-films of semiconductor wafer. This system and method analyze x-ray reflectivity data to determine transmission characteristics of thin-film layers. Based on these transmission characteristics the thickness of the thin-layer can be determined. Unlike some prior systems and methods, the system and method herein does not determine the thickness of the thin-film layer based on a fringe pattern in reflectivity for the thin-film layer. The fact that the system and method herein does not rely the fringe pattern is particularly advantageous in situations where the thin-film layer is of thickness which makes it very difficult to resolve the fringe pattern in the reflectivity data.

20 Claims, 4 Drawing Sheets

OTHER PUBLICATIONS

Wen–Li Wu et al., "Study of ultra–thin hydrogen silsesquioxane films using X–ray reflectivity," *Thin Solid Films*, vol. 312, 1998, pp. 73–77.

E.K. Lin et al., "Structure and Property Characterization of Porous Low–k Dielectric Constant Thin Films using X–ray Reflectivity and Small Angle Neutron Scattering," *Mat. Res. Soc. Symp. Proc.*, vol. 612, 2000[Materials Research Society], pp. D4.1.1–D4.1.8.

B.J. Bauer et al., "Structure and Property Characterization of Low–k Dielectric Porous Thin Films," Electronics Materials 30(4), pp. 304–308, 2001.

P. Boher et al., "Radio frequency sputtering of tungsten/tungsten nitride multilayers of GaAs," *J. Vac. Sci. Technol. A*, vol. 8, No. 2, Mar./Apr. 1990, pp. 846–849.

E. Chason et al., "*In situ* energy dispersive x–ray reflectivity measurements of H ion bombardment on $SiO_2$/Si and Si," *Appl. Phys. Lett.*, vol. 60, No. 19, May 11, 1992, pp. 2353–2355.

N. Awaji et al., "High–Accuracy X–ray Reflectivity Study of Native Oxide Formed in Chemical Treatment," *Jpn. J. Appl. Phys.*, vol. 34, 1995, pp. L1013–1016.

W.C. Johnson et al., "Rapid X–Ray reflectometry (XRR) metrology applied to Cu/low–k Damascene process development," *In Process Control and Diagnostics, Proceedings of SPIE*, vol. 4182, 2000, pp. 106–114.

B. Poumellec et al., "A new method to extract the X–ray absorption fine structures from the reflectivity spectra: application to the study of $(Ti.Nb)O_2$ amorphous solid solutions," *Physica B*, vol. 158, 1989, pp. 282–283.

* cited by examiner

US 6,507,634 B1

SYSTEM AND METHOD FOR X-RAY REFLECTOMETRY MEASUREMENT OF LOW DENSITY FILMS

RELATED APPLICATION

The present application claims the benefit of U.S. Provisional Application Serial No. 60/323,255, filed Sep. 19, 2001, titled X-RAY REFLECTOMETRY MEASUREMENT OF LOW DENSITY FILMS which is incorporated herein by reference.

TECHNICAL FIELD

The present invention relates to the field of measurement of materials used in the fabrication of semiconductor devices. Specifically, the present invention pertains to using transmission characteristics of thin-film layers disposed on a substrate to determine the thickness of the thin-film layer.

BACKGROUND

Semiconductor wafers typically include thin-films formed on semiconductor substrates. There is a need to be able to measure and analyze characteristics of these films. Previous systems have provided a way to analyze the thickness and density of thin-films disposed on semiconductor substrates using X-ray reflectometry (XRR). For example, U.S. Pat. No. 5,619,548 and PCT Publication W01/71325 A2 (referred to herein as the '325 application) discuss different aspects of XRR systems and are hereby incorporated by reference.

XRR systems of the prior art make use of the fact that x-rays reflected off of a thin-film disposed on a substrate are detected as having different characteristics depending on the x-ray's angle of reflection relative to the surface of the structure. FIG. 1 shows a view of a prior art XRR system for simultaneous measurements of the reflectivity over a range of angles. As shown in FIG. 1 a source 100 generates an x-ray beam 101 that is incident upon an x-ray reflector 102, which is typically a monochromator. X-rays are then focused upon the sample being evaluated 106 which is positioned on a supporting stage 104. X-rays incident upon the sample are reflected and then detected with a position-sensitive detector 108 (such as a photodiode array).

Reflected x-rays 110 are captured in the top half of the detector 108, while the incident beam 112 can be measured by lowering the stage and reading the bottom half of the detector. By properly normalizing the two profiles (as described in the '325 application) one can determine the reflectivity as a function of angle. Signals are generated by the detector 108, and the information contained in these signals is then used by the processor system 114 to analyze the reflectivity characteristics of the sample 106. The processor system 114 can then generate a display 116 to convey information about the sample 106 to user.

FIG. 2 shows a typical plot of angle-resolved XRR data, in a graph form which could be generated by the processor system 114. This type of graph depicts the efficiency with which monochromatic x rays are reflected from a sample, and this type of information can characterize the reflectivity of a thin-film disposed on a substrate. Specifically, FIG. 2 shows a graph for reflectivity of x-rays incident on a 358 Å cobalt thin film, on a substrate taken at 6.4 keV. The reflectivity signal shows a fringe pattern having peaks 206, and these peaks correlate to different reflection angles. It will be readily appreciated by one skilled in the art that as the thickness of the film increases the difference in the reflection angle between the peaks will decrease. For thin-films of sufficient thickness, prior systems may not be able to accurately resolve the fringe pattern, and as a result it may be difficult or impossible to determine the thickness of the thin-film. One approach for dealing with this problem is to modify the resolution of the system, but in general there is a limit to how much the resolution of the system can be increased, and further increasing the resolution of the system results in an increase in the amount of time it takes to make a measurement. (Aspects of one approach to varying the resolution of the system are disclosed in co-pending commonly assigned patent application Ser. No. 10/053,373 entitled X-RAY REFLECTANCE MEASUREMENT SYSTEM WITH ADJUSTABLE RESOLUTION, filed Oct. 24, 2001, which is incorporated herein by reference.)

One example of a semiconductor wafer structure where prior art XRR techniques are often unable to accurately determine the characteristics of a thin-film, is where a thin-film of porous $SiO_2$ is formed on a second film, or material, which is composed of a material which is denser than $SiO_2$. Using previous systems and methods it was often difficult, or impossible to accurately determine the thickness of the porous $SiO_2$ material, because in many applications the $SiO_2$ layer is thick enough that it produces a very narrow fringe pattern which is beyond the resolution of the system. What is needed is a system and method for accurately determining the thickness of a thin film layer where the thin film layer is such that it produces an fringe pattern that is cannot be accurately resolved using standard XRR systems.

SUMMARY

Prior XRR systems utilize fringe patterns in reflectivity data to determine the thickness of a thin-film layer. In general terms, the fringe pattern is caused by the interference of x-rays reflected at the several density interfaces present in a thin-film structure, such as for a thin-film layer on a substrate. Changes in the thickness of the thin-film layer will result in changes in fringe pattern.

In contrast with prior methods which focus on using the reflectivity information to determine a fringe pattern and then use this information to determine the thickness of the thin-film, the present method and system use reflectivity information to determine transmission characteristics of the thin-film layer. The transmission characteristics are then used to determine the thickness of the thin-film. A system and method which evaluates the transmission characteristics of the thin-film, as disclosed herein, can be used to determine the thickness of the thin-film structures which could not be determined using many prior systems which utilized fringe pattern analysis.

DETAILED DESCRIPTION

The system and method herein uses absorption characteristics of a thin-film to provide an analysis of XRR data that allows for the thickness·density product ($\rho \cdot T$), and thereby thickness information, of certain low-density thin films to be deduced from angle-resolved x-ray reflectometry (XRR) data. The method is applicable to low-density thin-films deposited on substrates, or additional thin-films, of a higher density.

Commercially important structures having these characteristics include a porous silicon dioxide $SiO_2$ interlayer dielectric deposited on silicon; and barium strontium titanate (BST) deposited on platinum; and silicon deposited on silicon-germanium alloy.

Figure 2:
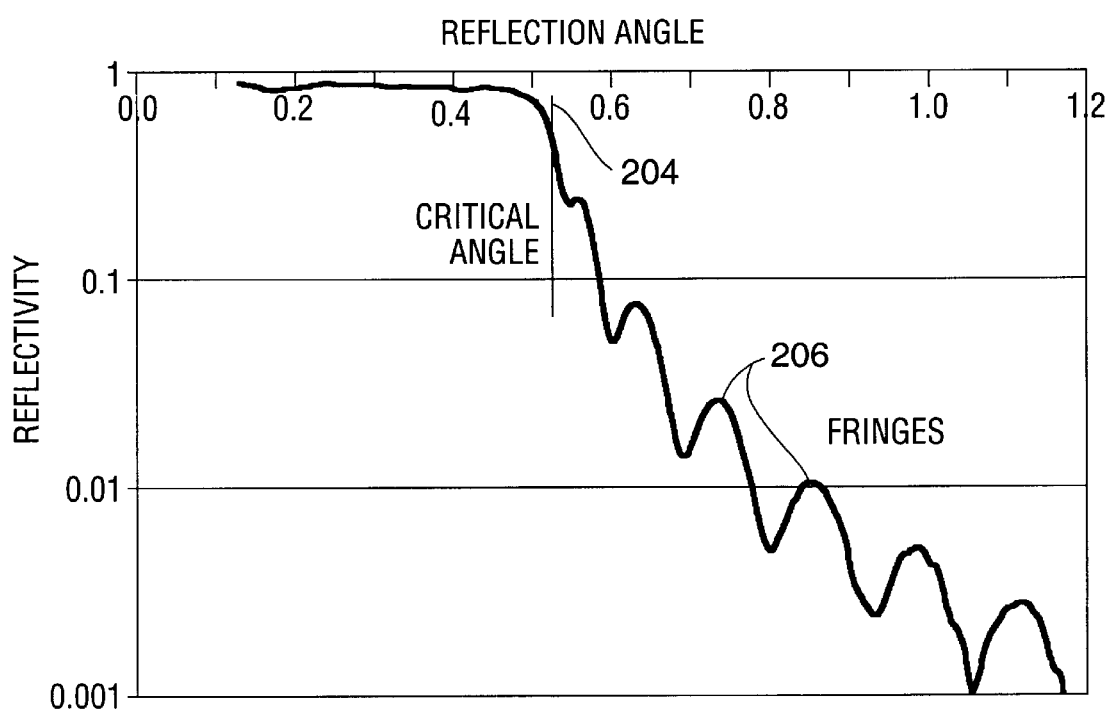
FIG. 2 is a graph showing the fringe profile for a thin film sample.

FIG. 2 shows XRR data which is utilized in prior systems. The locations of interference fringes 206 are used to deduce the thickness of a film. The rapid decrease of the efficiency of the reflection occurs at a "critical angle" 204. The critical angle is used to deduce the density of the film. For angles below the critical angle, the sample is nearly totally reflective for x rays. Above the critical angle, the rays penetrate into the film to some extent, and the reflectivity decreases. The value of critical angle scales with the density of the film, so that a low-density film will have a lower critical angle, and a higher density film, will have a higher critical angle. As will be seen below the method and system discussed herein takes advantage of the fact that the critical angle scales with the density of the film.

Figure 1:
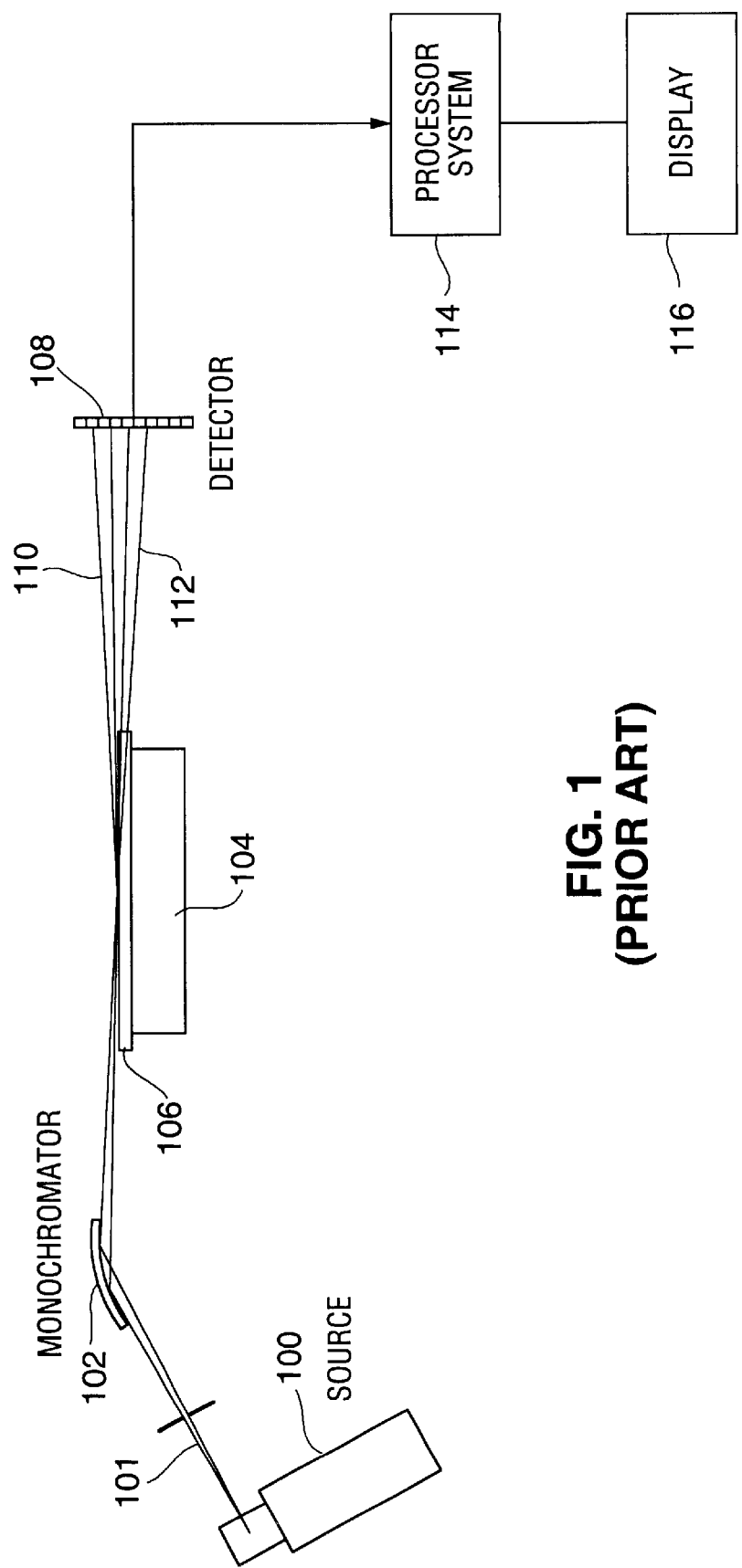
FIG. 1 shows an XRR system of the prior art.
Figure 3:
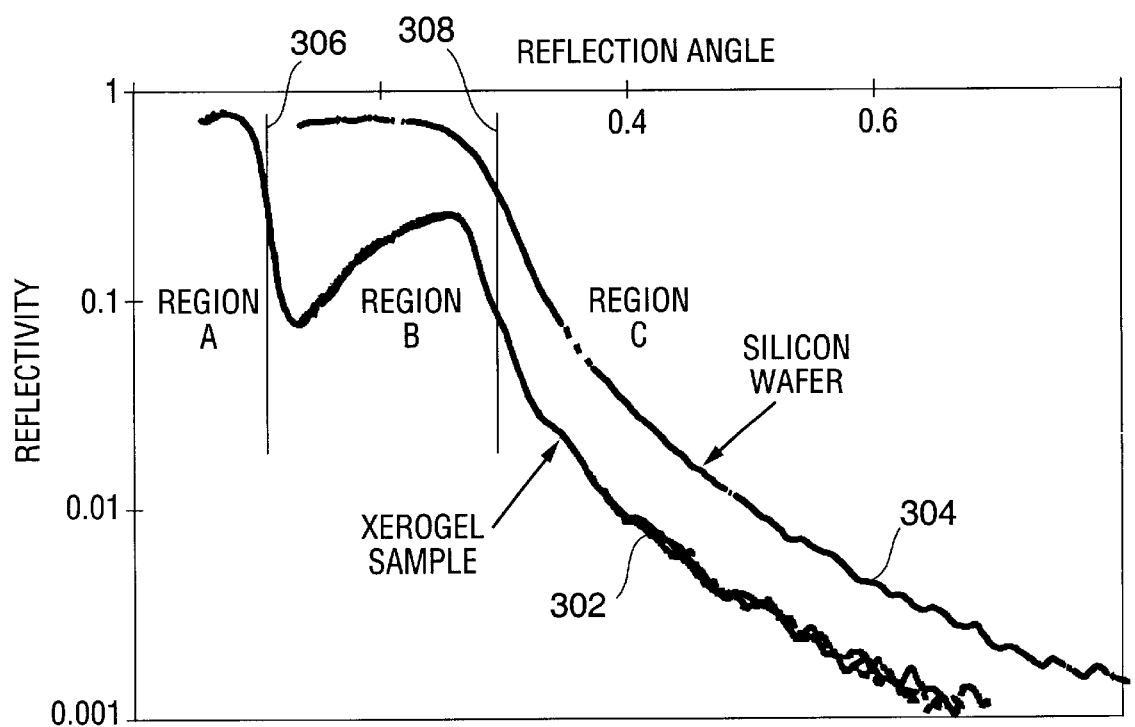
FIG. 3 is a graph showing the fringe profile for a thin film sample, where the thickness of the thin-film sample is such that the fringe pattern cannot be resolved using prior art techniques.

FIG. 3 shows XRR data for a different sample consisting of a thick porous $SiO_2$ film, sometimes referred to as Xerogel, deposited on a silicon substrate 302, and XRR data for a bare silicon substrate 304 is shown for comparison. The invention herein makes use of the fact that important information can be obtained by analyzing the reflectivity data presented in FIG. 3, and in similar graphs where a low-density film is deposited on top of a denser substrate or a denser thin-film. As shown in FIG. 3 there are two critical angles 306 and 308: where 306 corresponds to the critical angle for the $SiO_2$ layer, and 308 corresponds to the critical angle for the bare silicon. As discussed above, based on these critical angles the densities for the materials can be determined. In region A, below the critical angle 306 for $SiO_2$, the x-ray beam is nearly totally reflected. In region B, between the two critical angles 306 and 308, x-rays penetrate through the top film $SiO_2$, and reflect off of the substrate or bottom film, and re-emerge as an externally observable signal that is received by a detector 108 as shown in FIG. 1. In region C, above the substrate or bottom film critical angle 308, the reflectivity of the substrate decreases rapidly. In the data shown in FIG. 3, the $SiO_2$ film is too thick to produce resolvable interference fringes, and thus the $SiO_2$ film's thickness cannot be deduced using prior XRR data analysis. As one skilled in the art will appreciate, however, the density can be determined from the location of the critical angle (at approximately 0.1°) to be about 0.3 grams/cc.

Figure 4:
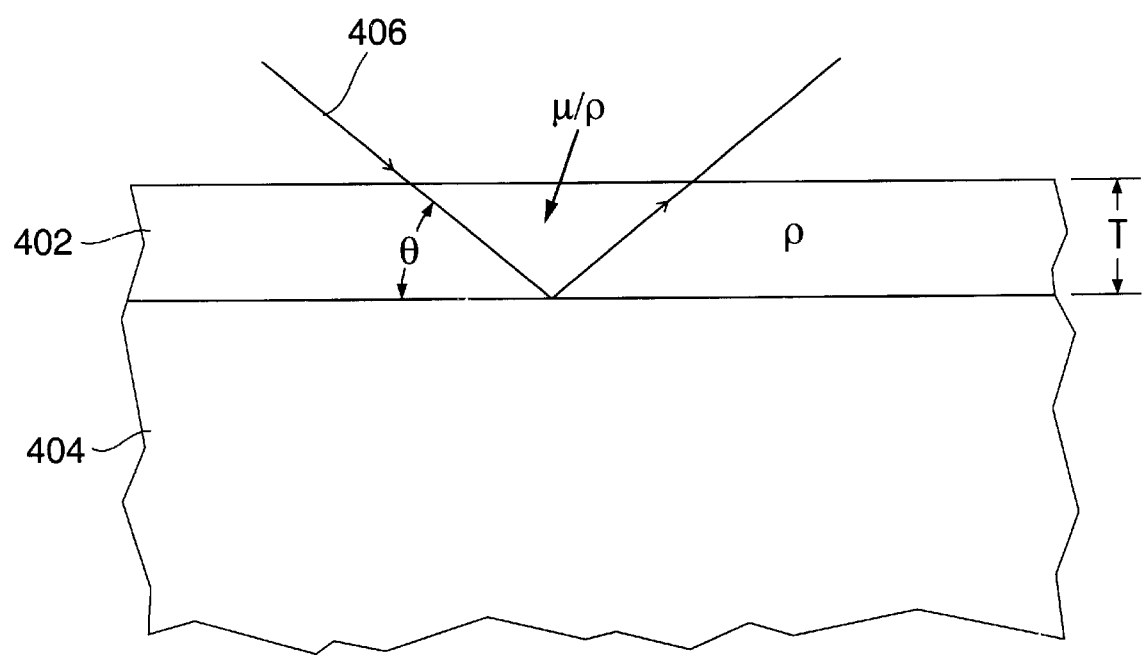
FIG. 4 shows a cross section of a sample being analyzed.

The invention uses information in the region between the two critical angles 306 and 308 (defined as region B above) to determine the thickness-density product of the low-density $SiO_2$ film, in a manner very different than the prior XRR data analysis methods. This analysis recognizes that if the substrate were left uncoated, then the observed reflectivity would have a value near unity in region B (i.e. the curve 302 would be the same as curve 304) and that the reflectivity is reduced below unity as a result of the absorption of x-rays in the low-density $SiO_2$ film. Essentially, the low-density film functions as an x-ray filter that attenuates the x-ray beam twice, once as it propagates down to the substrate and again as it is reflected by the substrate. This effect is shown graphically in FIG. 4, where the incident x-ray beam 406 penetrates into the $SiO_2$ layer 402 and travels through the layer 402 until it is incident with the layer 404 which is denser, and hence has a higher critical angle. Due to the fact that the layer 404 has a higher critical angle it will continue to reflect the x-rays until they reach the higher critical angle of the layer 404. Thus, the reflected x-ray will be travel back through the $SiO_2$ layer 402 and be detected by the detector. As the angle of incidence with the surface of the film increases, the distance which the x-ray travels through the film is reduced which results in the reflected signal increasing in strength as the angle of incidence increases. This increase in strength is directly related to the fact that the distance which the x-ray 406 travels through the $SiO_2$ layer 402 is determined by the equation:

Distance x-ray travel in layer $402=(2T)/\sin \Theta$;

where T is the thickness of the layer 402, and $\Theta$ is the angle of incidence of the x-ray 406 with the layer 404. The fact that the reflectivity increases as the angle increases in the region B, is reflected in FIG. 3. Specifically, the strength of the reflected x-rays increases in Region B as the reflection angle increases. Once the critical angle of the material 404 is reached than the reflectivity begins to rapidly decrease as the x-ray begins to penetrate into layer 404.

This attenuation in region B can be modeled by the Lambert-Beers transmission law: $I/I_0 = \exp(-2\mu/\rho \cdot \rho T/\sin \theta)$ to yield a calculation, independent of a fringe pattern analysis, of the thickness-density product, $\rho \cdot T$ of the layer of $SiO_2$ 402. Specifically, to solve for T (the thickness) one would take the natural log of the above equation, thereby reducing it to a linear equation. The reflectivity data for region B would then be used in connection with the resulting linear equation: $\ln(I/I_0) = -2\mu/\rho \cdot \rho T/\sin \theta$, to determine a value for T. As one of skill the art would appreciate a least squares fitting algorithm can be used in conjunction with the linear equation and the reflectivity data to determine a value for the thickness T. Further, it may be desirable to use a theoretical model of the sample and to calculate its response to the incident x-rays. The result can be compared to the measured data using a curve fitting minimization algorithm to determine a value for T.

Use of the Lambert-Beers transmission law is in contrast with conventional XRR data analysis, which is based on the Fresnel equations where $\sin^2 \Theta_n = \sin^2 \Theta_c + [(n+\frac{1}{2})^2 (\lambda/2T)^2]$, $n=1,2,3,4...$; where $\Theta_n$ is reflection angle corresponding to a peak of a fringe and $\lambda$ is the wavelength of the probe beam; $\Theta_c$ is the critical angle; n corresponds to the order number of the fringe; and T is the thickness of the film. Where the fringe pattern can be resolved as in FIG. 1, the above Fresnel equation can be used to solve for T, as all of the other parameters can be determined.

In contrast in region B of FIG. 2 the peaks of the fringe pattern can not be resolved, so the $\Theta_n$ angle corresponding to peaks of a fringe pattern cannot be ascertained, and without knowing this value one cannot solve for the unknown T (the thickness of the film). To deal with this limitation of prior systems, the value of $I/I_0$ can be used in the Lambert-Beer equation, where $I/I_0$ is the observed transmission ratio of the low-density film, which is determined from the graph of FIG. 3 as the ratio of the expected reflectivity 304 of a material 404 without the top layer of film 402 to the reflectivity measured 302 with the film 402 disposed on the material 404, in region B. The expected reflectivity of the material 404 can be determined based on modeling or referring to tabulated data for the expected reflectivity of the material 404, or it can be obtained by actually measuring semiconductor wafer having a top layer defined by material 404. A third alternative would be to assume that material 404 is totally reflective below the critical angle for the material 404. Regardless of which of these methods is used for determining a value for reflectivity of the material 404, the concept is the same. Herein, this approach, which could be implemented using any of the above methods, is described as comparing the reflectivity of the wafer with the thin-film layer with the reflectivity of a reference wafer, with the reflectivity of the reference wafer defining 10.

The value $\mu/\rho$ is the mass absorption coefficient of the low-density film 404. The mass absorption coefficient of the low-density film is determined by the composition of the film. Knowing the composition of the film one can refer to tabulated data to determine this value. The value $\Theta$ is the refraction corrected angle for the propagation angle in the film, which can be determined knowing the material of the film and the angle of reflection of the detected probe beam. The value of density, $\rho$, can be determined based on the location of the critical angle. The thickness T can be determined by solving the equation $I/I_0 = \exp(-2\,\mu/\rho \cdot \rho T/\sin \theta)$ for T. Thus, using the ratio of $I/I_0$ the value of T can be determined by the method and system of the present of the present invention where using prior art systems one could not determine this value because the peaks of the fringe pattern could not be resolved. Further, even where the resolution of a prior art system might be adjusted so that the fringe pattern could be determined, the present invention allows for determining the thickness without the need to increase the resolution of the system, which would result in increasing the amount of time needed to make the measurement. Thus, using the Lambert-Beers absorption law rather than the Fresnel equations, and using reflectivity data $I/I_0$ below the critical angle which in the past was ignored, the new measurement method and system is able to extract structural information characterizing a thin-film structure, where such information could frequently not be obtained in prior XRR systems.

To implement the system and method disclosed herein one could use a system very similar to that shown in FIG. 1, but the processor system would need to programmed such that it utilized the equations and relationship discussed herein to determine thickness of a low density film using the transmission properties of the thin-film.

While the method and apparatus of the present invention has been described in terms of its presently preferred and alternate embodiments, those skilled in the art will recognize that the present invention may be practiced with modification and alteration within the spirit and scope of the appended claims. The specifications and drawings are, accordingly, to be regarded in an illustrative rather than a restrictive sense. Further, even though only certain embodiments have been described in detail, those having ordinary skill in the art will certainly understand that many modifications are possible without departing from the teachings thereof. All such modifications are intended to be encompassed within the following claims.

What is claimed is:

1. In a system for measuring characteristics of a semiconductor wafer having a thin-film layer, and a first material on which the thin-film layer is formed, a method for analyzing the thin-film layer comprising:

measuring a plurality x-rays reflected off the semiconductor wafer to determine a reflectivity of the semiconductor wafer;

determining a transmission characteristic of the thin-film layer based on the reflectivity of the semiconductor wafer; and determining a thickness of the thin-film layer based on the transmission characteristic of the thin-film layer.

2. The method of claim 1 further comprising analyzing the reflectivity of the semiconductor wafer between a first critical angle and a second critical angle to determine the transmission characteristic of the thin-film layer.

3. The method of claim 1, wherein the determining of the transmission characteristic of the thin-film layer includes:

determining the ratio of the reflectivity of the semiconductor wafer having the thin-film layer formed on the first material to a reflectivity of a reference semiconductor wafer.

4. The method of claim 1, wherein the determining the thickness of the thin-film layer based on the transmission characteristic of the thin-film layer, includes:

determining the mass absorption coefficient for the thin-film layer based on a composition of the thin-film layer.

5. The method of claim 1, wherein the determining the thickness of the thin-film layer based on the transmission characteristic of the thin-film layer, includes:

identifying an angle of reflection, $\Theta$, for an x-ray reflected off the first material on which the thin-film layer is disposed.

6. The method of claim 1, wherein the determining the thickness of the thin-film layer based on the transmission characteristic of the thin-film layer, includes:

using a critical angle of the thin-film layer to determine the density of the thin-film layer.

7. The method of claim 1, wherein the determining the thickness of the thin-film layer based on the transmission characteristic of the thin-film layer, includes:

determining a ratio of the reflectivity of the semiconductor wafer with the thin-film layer relative to a reflectivity of a reference semiconductor wafer having a top layer which includes the first material;

determining the mass absorption coefficient for the thin-film layer based on a composition of the thin-film layer; identifying an angle of reflection, $\Theta$, corresponding to an x-ray reflected off the first material on which the thin-film layer is disposed; and using a critical angle to determine a density of the thin-film layer.

8. The method of claim 1, wherein the determining the thickness of the thin-film layer based on the transmission characteristic of the thin-film layer, further comprises, using the following equation to determine the thickness of the thin-film layer:

$$I/I_0 = \exp(-2\mu/\rho \cdot \rho T/\sin \theta);$$

where $I/I_0$ is the ratio of the reflectivity of the semiconductor wafer with the thin-film layer relative to the reflectivity of a reference semiconductor wafer having a top layer which includes the first material;

where $\mu/\rho$ is mass absorption coefficient for the thin-film layer;

where $\rho$ is the density of the thin-film layer;

where $\theta$ is the angle of reflection off the first material on which the thin-film layer is formed; and where T is the thickness of the thin-film layer.

9. A method for using x-ray reflectivity data of a semiconductor wafer to determine a thickness of a thin-film layer of the semiconductor wafer, where the thin-film layer is formed on a first material of the semiconductor wafer, the method comprising:

determining a transmission characteristic of the thin-film layer using x-ray reflectivity data of the semiconductor wafer; and determining a thickness of the thin-film layer based on the transmission characteristic of the thin-film layer.

10. The method of claim 9, wherein the determining the transmission characteristic of the thin-film includes:

determining a ratio of the reflectivity of the semiconductor wafer with the thin-film layer relative to the reflectivity of a reference semiconductor wafer.

11. The method of claim 9, wherein the determining the thickness of the thin-film layer based on the transmission characteristic of the thin-film layer, includes:

determining a mass absorption coefficient for the thin-film layer based on a composition of the thin-film layer.

12. The method of claim 9, wherein the determining the thickness of the thin-film layer based on the transmission characteristic of the thin-film layer,includes:

determining the density of the thin-film layer based on a critical angle of reflection for the thin-film layer.

13. The method of claim 9, wherein the determining the thickness of the thin-film layer based on the transmission characteristic of the thin-film layer, further comprises:

determining a ratio of the reflectivity of the semiconductor wafer with the thin-film layer to the reflectivity of a reference semiconductor wafer;

determining the mass absorption coefficient for the thin-film layer based on a composition of the thin-film layer;

identifying an angle of reflection $\Theta$ for an x-ray reflected off the first material on which the thin-film layer is disposed; and determining a density of the thin-film layer based on a critical angle of the thin-film layer.

14. The method of claim 9, wherein the determining the thickness of the thin-film layer based on the transmission characteristic of the thin-film layer, further comprises, using the following equation to determine the thickness of the thin-film layer:

$$I/I_0 = \exp(-2\mu/\rho \cdot \rho T/\sin \theta);$$

where $I/I_0$ is the ratio of the reflectivity of the semiconductor wafer with the thin-film layer relative to the reflectivity of a reference semiconductor wafer having a top layer which includes the first material;

where $\mu/\rho$ is mass absorption coefficient for the thin-film layer based on a composition of the thin-film layer;

where $\rho$ is the density of the thin-film layer;

where $\theta$ is the angle of reflection off the first material on which the thin-film layer is disposed; and where T is the thickness of the thin-film layer.

15. A system for measuring properties of a semiconductor wafer having a thin-film layer formed on a first material, the system comprising:

a detector positioned to sense x-rays reflected off the semiconductor wafer; and a processor system coupled to the detector, wherein the processor system is programmed to determine a transmission characteristic of the thin-film layer based on x-rays sensed by the detector, and to calculate a thickness of the thin-film layer based on the transmission characteristic.

16. The system of claim 15, wherein the processor system determines the transmission characteristic by determining a ratio of a reflectivity of the semiconductor wafer to a reflectivity of a reference semiconductor wafer.

17. The system of claim 16, wherein the reference semiconductor wafer has a top layer including the first material.

18. The system of claim 16, wherein the ratio is determined using reflectivity data between a first critical angle for the thin-film layer and a second angle which is a critical angle for the first material.

19. A method of analyzing x-ray reflectivity data obtained by measuring the intensity of x-rays reflected off a sample corresponding to a plurality of angles of incidence with the sample, said sample including a top layer having a density less than an underlying material upon which the top layer is formed, said method comprising:

evaluating the absorption of x-rays caused by the top layer, at angles of incidence between a critical angle for the top layer and a critical angle for the underlying material; and determining a characteristic of the top layer based on the evaluation.

20. The method of claim 19, wherein the characteristic which is determined is the thickness the top layer.

* * * * *